United States Patent
Margalit

(10) Patent No.: US 11,547,606 B2
(45) Date of Patent: Jan. 10, 2023

(54) ENHANCING OPTICAL DETECTION OF MICRO BUBBLES BY LASER PULSE EXPANSION

(71) Applicant: LUTRONIC VISION INC., Burlington, MA (US)

(72) Inventor: Mordehai Margalit, Zikhron Ya'akov (IL)

(73) Assignee: LUTRONIC VISION INC., Burlington, MA (US)

( * ) Notice: Subject to any disclaimer, the term of this patent is extended or adjusted under 35 U.S.C. 154(b) by 0 days.

(21) Appl. No.: 16/758,241

(22) PCT Filed: Oct. 22, 2017

(86) PCT No.: PCT/US2017/057768
§ 371 (c)(1),
(2) Date: Apr. 22, 2020

(87) PCT Pub. No.: WO2019/078902
PCT Pub. Date: Apr. 25, 2019

(65) Prior Publication Data
US 2020/0261268 A1 Aug. 20, 2020

(51) Int. Cl.
*A61F 9/008* (2006.01)

(52) U.S. Cl.
CPC .......... *A61F 9/0084* (2013.01); *A61F 2009/00844* (2013.01)

(58) Field of Classification Search
CPC ......... A61F 9/0084; A61F 2009/00844; A61B 18/18; A61B 18/20; A61B 18/04
See application file for complete search history.

(56) References Cited

U.S. PATENT DOCUMENTS

| | | | |
|---|---|---|---|
| 5,307,369 A * | 4/1994 | Kimberlin | H01S 3/07 372/107 |
| 8,366,704 B2 | 2/2013 | Lin et al. | |
| 8,562,595 B2 * | 10/2013 | Plunkett | A61F 9/008 606/4 |
| 8,968,280 B2 * | 3/2015 | Lin | A61F 9/00821 606/4 |
| 9,291,774 B1 * | 3/2016 | Adamovsky | G02B 6/29341 |
| 2012/0029490 A1 | 2/2012 | Lin et al. | |

OTHER PUBLICATIONS

International Search Report and Written Opinion for International Application No. PCT/US2017/057768 dated Jan. 8, 2018, pp. 10.
Lachaine, R., et al., "Effect of pulse duration on plasmonic enhanced ultrafast laser-induced bubble generation in water," Applied Physics A—Materials Science & Processing, vol. 112, Issue 1, pp. 1-4 (Sep. 6, 2012).

* cited by examiner

Primary Examiner — Carl H Layno
Assistant Examiner — Aya Ziad Bakkar

(57) ABSTRACT

In some examples, a laser-based ophthalmological surgical system (hereinafter "system") includes a therapeutic radiation source configured to emit therapeutic radiation at a first intensity during a therapeutic portion and to emit probe radiation with a second intensity which is less than the first intensity during a probe portion. The system may also include one or more optical elements configured to direct the therapeutic portion and the probe portion into an eye of a patient and to collect reflected radiation from the eye of the patient. The reflected radiation may be indicative of dynamics of microbubbles in the cells of the eye of the patient.

21 Claims, 12 Drawing Sheets

ENHANCING OPTICAL DETECTION OF MICRO BUBBLES BY LASER PULSE EXPANSION

CROSS-REFERENCE

This patent application is section 371 nationalization of PCT Application No. PCT/US2017/057768 filed Oct. 22, 2017, which application is incorporated herein by specific reference in its entirety.

BACKGROUND

Unless otherwise indicated herein, the materials described herein are not prior art to the claims in the present application and are not admitted to be prior art by inclusion in this section.

Therapeutic radiation may be administered to an eye of a patient to treat various conditions of the eye that may negatively affect vision. It may be difficult to accurately measure an exposure level of the eye to the therapeutic radiation, which can damage the eye at excess exposure levels.

SUMMARY

Techniques described herein generally relate to a system and methods of improved optical detection and monitoring of microbubbles formed during therapeutic radiation. In an example embodiment, a method of therapeutic radiation dosimetry is described. The method may include irradiating an eye of a patient with radiation pulses, each of the radiation pulses comprising a therapeutic portion with at least a first intensity followed by a probe portion with a second intensity less than the first intensity; wherein each therapeutic portion of each of the radiation pulses causes microbubbles to form on melanosomes of retinal pigment epithelial (RPE) cells of the eye of the patient. The method may also include collecting reflected radiation pulses from the eye of the patient, each of the reflected radiation pulses comprising a reflected therapeutic portion and a reflected probe portion. The method may also include generating a photocurrent from the collected reflected radiation pulses, the photocurrent being indicative of dynamics of the microbubbles in the RPE cells of the eye of the patient.

In another example embodiment, a laser-based ophthalmological surgical system. The system may include a therapeutic radiation source configured to emit at least therapeutic portions of radiation pulses, wherein each of the therapeutic portions has at least a first intensity and wherein each of the therapeutic portions is configured to cause microbubbles to form on melanosomes of retinal pigment epithelial (RPE) cells of an eye of a patient. The system may also include one or more optical elements configured to direct the radiation pulses into the eye of the patient and to collect reflected radiation pulses from the eye of the patient. Each of the radiation pulses may include both a therapeutic portion of the therapeutic portions followed by a probe portion with a second intensity less than the first intensity. Each of the reflected radiation pulses may include a reflected therapeutic portion and a reflected probe portion. The system may also include a photodetector configured to receive the reflected radiation pulses from the one or more optical elements and to generate from the reflected radiation pulses a photocurrent indicative of dynamics of the microbubbles in the RPE cells of the eye of the patient. In some embodiments, a method of therapeutic radiation dosimetry to an eye of a patient can include: irradiating the eye of the patient with radiation pulses, wherein each radiation pulse includes a therapeutic portion with at least a first intensity followed by a probe portion with a second intensity less than the first intensity, wherein each therapeutic portion of each radiation pulse is configured to cause microbubbles to form on melanosomes of retinal pigment epithelial (RPE) cells of the eye of the patient; collecting reflected radiation pulses from the eye of the patient, wherein each reflected radiation pulse includes a reflected therapeutic portion and a reflected probe portion; and generating a photocurrent from the collected reflected radiation pulses, the photocurrent being indicative of dynamics of the microbubbles in the RPE cells of the eye of the patient.

In some embodiments, the method can include at least one of: providing the therapeutic portion of each radiation pulse to the eye during the irradiating for a duration of about two microseconds or less; or providing the probe portion of each radiation pulse to the eye during the irradiating for a duration in a range from about two to about four microseconds.

In some embodiments, the method can include providing each radiation pulse to have the probe portion with the second intensity in a range from $\frac{1}{100}$ to $\frac{1}{20}$ of the first intensity of the therapeutic portion.

In some embodiments, the method can include modulating a therapeutic radiation source with a modulation signal that includes alternately a first signal level and a second signal level that is lower than the first signal level, wherein: the first signal level is configured to cause the therapeutic radiation source to emit the therapeutic portion of each radiation pulse; and the second signal level is configured to cause the therapeutic radiation source to emit the probe portion of each radiation pulse.

In some embodiments, the method can include: modulating a therapeutic radiation source with a modulation signal configured to cause the therapeutic radiation source to emit the therapeutic portion of each radiation pulse; and optically coupling the therapeutic radiation source to a resonant cavity that is configured to emit the probe portion of each radiation pulse following the therapeutic portion; and directing both the therapeutic portion emitted by the therapeutic radiation source and the probe portion emitted by the resonant cavity into the eye of the patient. In some embodiments, the method can include optically coupling a therapeutic radiation source that emits the radiation pulses into a resonant cavity by optically coupling the therapeutic radiation source into a Fabry-Pérot etalon.

In some embodiments, the method can include optically coupling a therapeutic radiation source that emits the radiation pulses into a Fabry-Pérot etalon having end mirrors each with a reflectivity greater than 99%.

In some embodiments, the method can include optically coupling a therapeutic radiation source that emits the radiation pulses into a resonant cavity by optically coupling the therapeutic radiation source into a spherical resonant cavity that supports whispering gallery modes.

In some embodiments, a laser-based ophthalmological surgical system can include: a therapeutic radiation source configured to emit radiation pulses, wherein each radiation pulse includes a therapeutic portion with at least a first intensity followed by a probe portion with a second intensity less than the first intensity, wherein the therapeutic portion is configured to cause microbubbles to form on melanosomes of retinal pigment epithelial (RPE) cells of an eye of a patient; one or more optical elements configured to direct the radiation pulses into the eye of the patient and to collect reflected radiation pulses from the eye of the patient, wherein each reflected radiation pulse includes a reflected therapeutic portion and a reflected probe portion; and a photodetector configured to receive the reflected radiation pulses from the one or more optical elements and to generate from the reflected radiation pulses a photocurrent indicative of dynamics of the microbubbles in the RPE cells of the eye of the patient.

In some embodiments, the laser-based ophthalmological surgical system can include the therapeutic radiation source that is configured to emit the radiation pulses that include at least one of: the therapeutic portion of each radiation pulse includes a duration of two microseconds or less; or the probe portion of each radiation pulse includes a duration in a range from about two to four about microseconds. In some aspects, therapeutic radiation source is configured to emit the probe portion with the second intensity in a range from $\frac{1}{100}$ to $\frac{1}{20}$ of the first intensity of the therapeutic portion.

In some embodiments, the laser-based ophthalmological surgical system can include a modulation circuit operably coupled to the therapeutic radiation source and configured to modulate the therapeutic radiation source with a modulation signal to cause the therapeutic radiation source to emit the radiation pulses.

In some embodiments, the laser-based ophthalmological surgical system can include a modulation circuit configured to provide a modulation signal that alternates between a first signal level and a second signal level that is lower than the first signal level, wherein: the first signal level is configured to cause the therapeutic radiation source to emit the therapeutic portion of each radiation pulse; and the second signal level is configured to cause the therapeutic radiation source to emit the probe portions of each radiation pulse.

In some embodiments, the laser-based ophthalmological surgical system can include a resonant cavity optically coupled to the therapeutic radiation source and configured to receive the therapeutic portion of each radiation pulse and to emit the probe portion following the therapeutic portion.

In some embodiments, the laser-based ophthalmological surgical system can include a resonant cavity optically coupled to the therapeutic radiation source, wherein the resonant cavity includes a Fabry-Pérot etalon.

In some embodiments, the laser-based ophthalmological surgical system can include a resonant cavity that includes a Fabry-Pérot etalon optically coupled to the therapeutic radiation source, wherein the Fabry-Pérot etalon comprises end mirrors each with a reflectivity greater than 99%. In some embodiments, the laser-based ophthalmological surgical system can include a resonant cavity that includes a Fabry-Pérot etalon optically coupled to the therapeutic radiation source, wherein the Fabry-Pérot etalon has an effective length equal to $c*t_{pulse}$, wherein c is the speed of light in a vacuum and $t_{pulse}$ is a duration of each radiation pulse in a range from about two to about four microseconds.

In some embodiments, the laser-based ophthalmological surgical system can include a resonant cavity optically coupled to the therapeutic radiation source, wherein the resonant cavity includes a spherical resonant cavity that supports whispering gallery modes.

In some embodiments, the laser-based ophthalmological surgical system can include a processor communicatively coupled to the photodetector and the therapeutic radiation source, wherein the processor is configured to perform or control performance of the system to: determine an exposure level of the eye of the patient to the radiation pulses based on the generated photocurrent; and terminate exposure of the eye of the patient to the radiation pulses in response to the exposure level reaching a threshold exposure level.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1A:
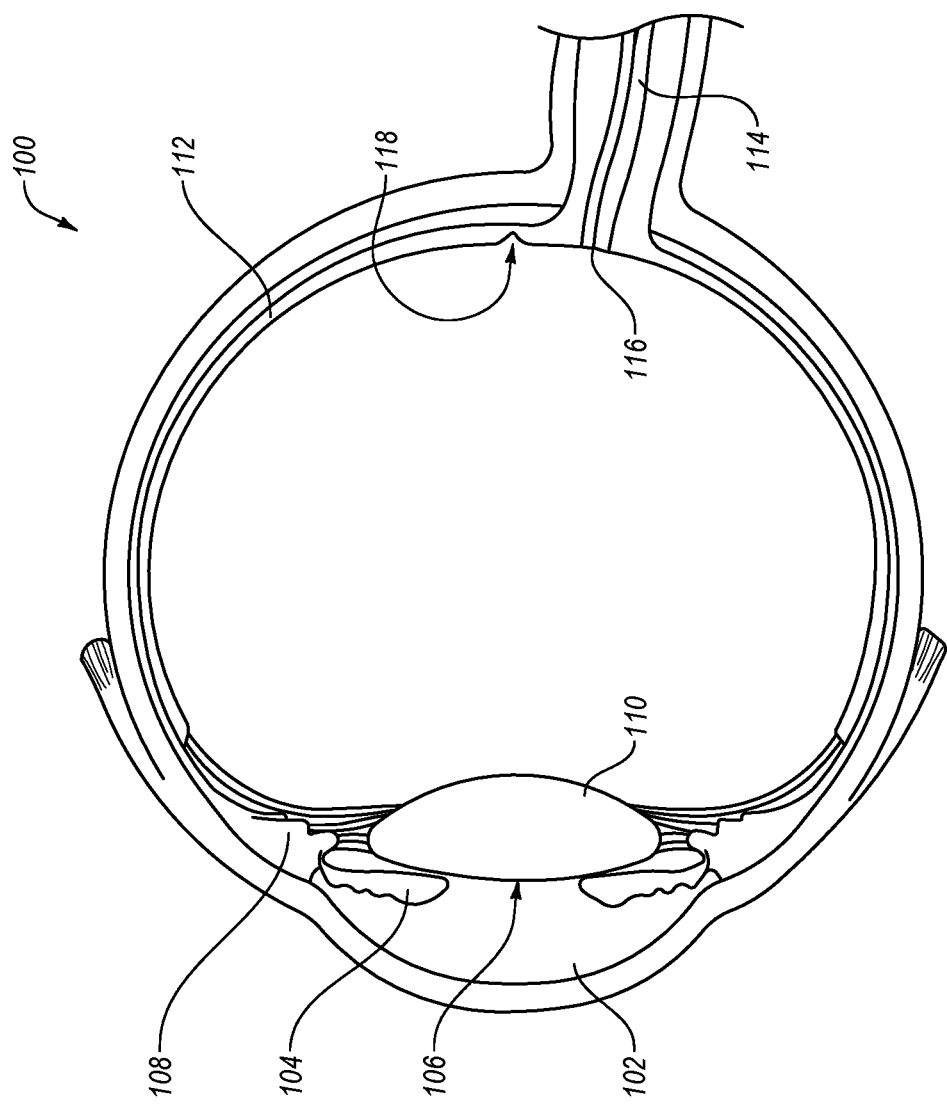
FIG. 1A is a cross-sectional view of an example human eye (hereinafter "eye")

This disclosure is generally drawn to methods, apparatus, systems, devices, and computer program products related to enhancing the optical detection of microbubbles formed during radiation by expanding the application of the laser pulse.

A laser-based ophthalmological surgical system (hereinafter "system") in accordance with the present disclosure may include a therapeutic radiation source and a probe radiation source. The therapeutic radiation source may emit therapeutic radiation, which may be directed to a target area of an eye of a patient. The therapeutic radiation may induce a change in the target area of the eye of the patient, such as formation and/or bursting of microbubbles, which may be measured optically. The probe radiation source may emit probe radiation which may be directed to the target area of the eye of the patient, and which may be reflected by the target area of the eye of the patient. The probe radiation may have a different wavelength than the therapeutic radiation. The system may also include one or more optical elements configured to direct the therapeutic radiation and the probe radiation into the eye of the patient and to collect reflected probe radiation from the eye of the patient. The system may also include a photodetector or other means of collecting reflected radiation pulses from the eye of the patient, the reflected radiation pulses including to a reflected therapeutic portion corresponding to the reflection of the therapeutic radiation and a reflected probe radiation corresponding to the reflection of the probe radiation. The photodetector or other means of collecting the reflected radiation pulses may also generate a photocurrent which is indicative of dynamics of the microbubbles in the RPE cells of the eye of the patient. The photocurrent may then be analyzed to identify the existence and characteristics of microbubbles in the RPE cells of the eye of the patient. In some instances, the depth of individual microbubbles in the RPE cells of the eye of the patient may be determined.

When a laser is targeted to the retina of a user, the melanosomes in the RPE absorb the energy resulting in an increase in temperature and the formation of micro-bubbles, which damage the RPEs. In order to avoid excessive damage during the laser irradiation process, it is important to monitor the RPEs for the creation of the micro-bubbles as excessive laser radiation after the formation of micro-bubbles can result in RPE damage and damage to other retinal structures, possibly leading to the formation of scotoma. The system may include analyzing the photocurrent to identify the existence, size, depth, or other characteristics of micro-bubbles so as to provide improved laser-based ophthalmological surgery.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

FIG. 1A is a cross-sectional view of an example human eye (hereinafter "eye") 100, arranged in accordance with at least one embodiment described herein. The eye 100 may include a cornea 102, an iris 104, a pupil 106, a ciliary body 108, a lens 110, a retina 112, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

As illustrated in FIG. 1A, the retina 112 includes an optic disc 116, sometimes referred to as the "blind spot", and a macula 118 temporal to the optic disc 116.

Figure 1B:
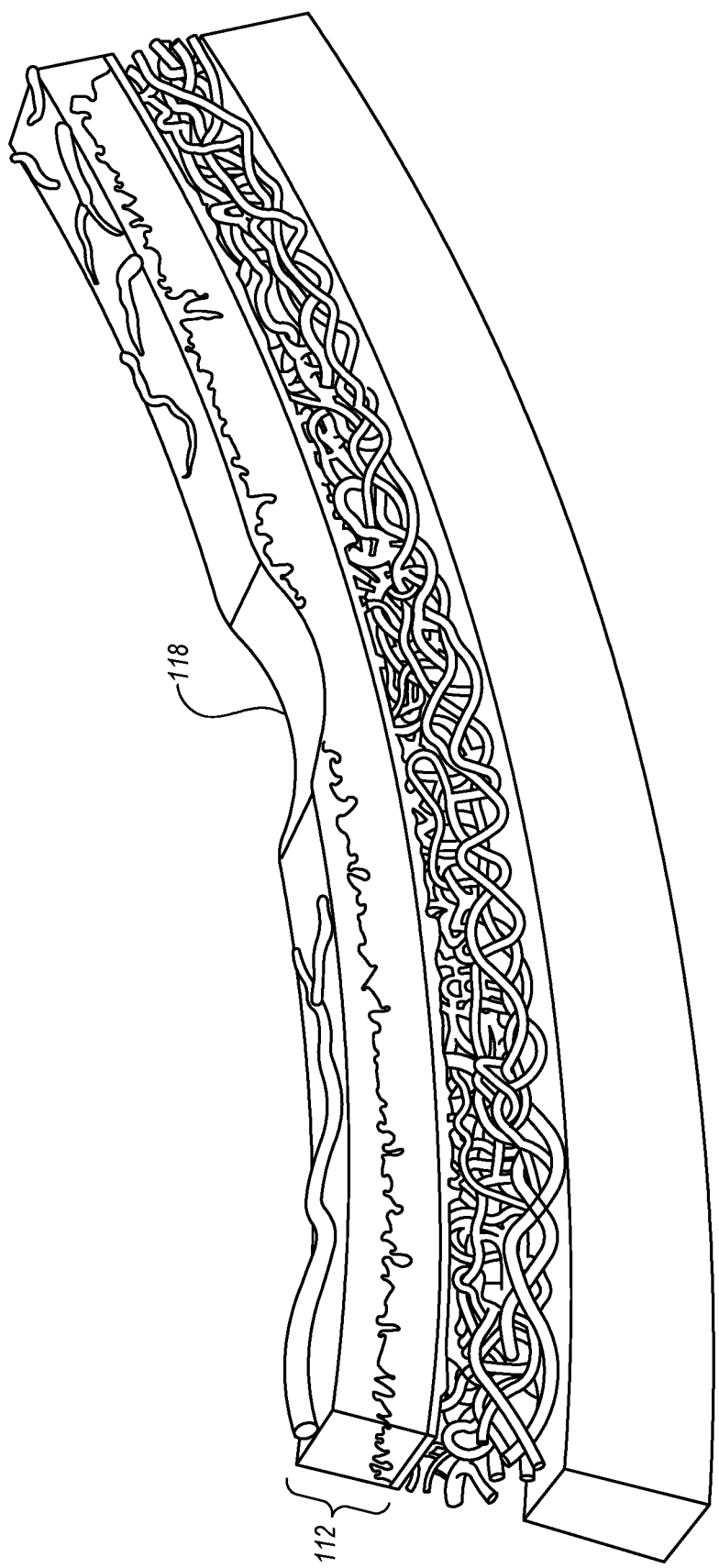
FIG. 1B is a cross-sectional perspective view of a portion of a retina and macula of FIG. 1A.

FIG. 1B is a cross-sectional perspective view of a portion of the retina 112 and the macula 118 of FIG. 1A, arranged in accordance with at least one embodiment described herein.

Figure 1C:
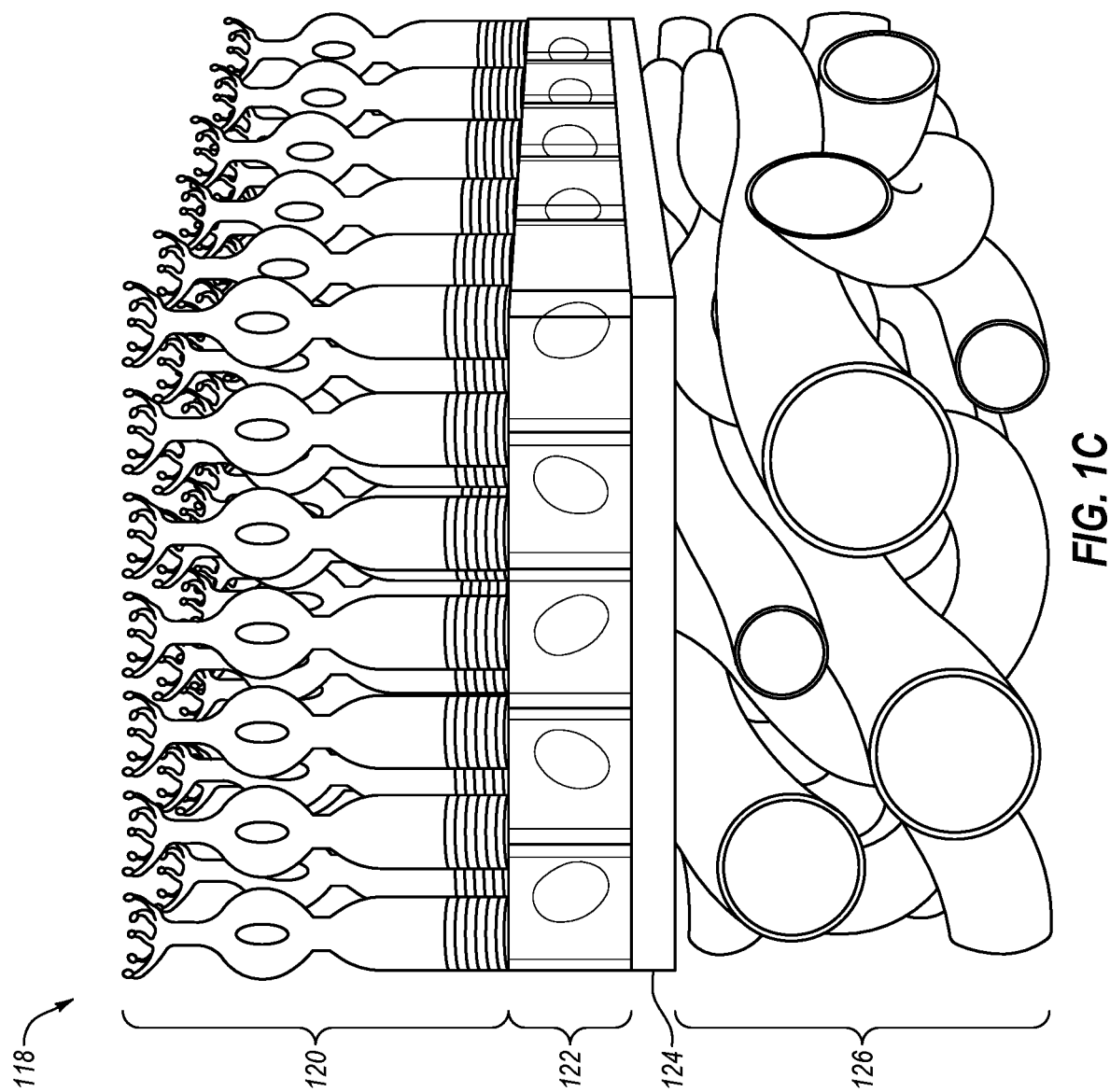
FIG. 1C is a cross-sectional perspective view of a portion of the macula of FIG. 1B.

FIG. 1C is a cross-sectional perspective view of a portion of the macula 118 of FIG. 1B, arranged in accordance with at least one embodiment described herein. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, age-related macular degeneration (AMD) may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be diabetic macular edema (DME). In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be central serous chorioretinopathy (CSC). In CSC, leakage of fluid accumulates under the central macula 118, resulting in blurred or distorted vision which may progressively decline with each recurrence.

Some embodiments described herein include a laser-based ophthalmological surgical system that includes a therapeutic radiation source configured to emit therapeutic radiation to treat AMD, DME, CSC, and/or other conditions of the eye 100. In general, the therapeutic radiation may be absorbed by RPE cells 122 targeted with the therapeutic radiation. Specifically, the therapeutic radiation may be absorbed by melanin or other chromophore in the RPE cells 122. The absorbed therapeutic radiation may be converted to heat, which may lead to formation of microbubbles in the RPE cells 122. The microbubbles may burst or otherwise destroy RPE cells 122. By targeting degraded RPE cells included in the RPE cells 122, the degraded RPE cells can be destroyed to prevent them from causing further damage.

According to some embodiments, such laser-based ophthalmological surgical systems may use real-time feedback to detect RPE damage and stop therapeutic radiation automatically based on the feedback prior to excessively damaging the targeted RPE cells 122. In an example embodiment, the therapeutic radiation is administered to the targeted RPE cells 122 in pulses with a pulse duration in a range from 1.6 microseconds to 6 microseconds.

As is described more fully below, the pulse may include two portions, including a therapeutic radiation portion with a pulse duration in a range from 1.6 to 1.8 microseconds, which is followed by a therapeutic portion, with a duration in the range of 2.2 to 4.2 microseconds. The administration of the therapeutic radiation portion may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. The administration of the therapeutic pulses may be terminated in response to the feedback indicating a maximum exposure to the therapeutic radiation. In other embodiments, the pulse frequency of the therapeutic radiation may be greater than 200 Hz.

The therapeutic radiation may in some embodiments be generally more effective at treating conditions of the eye at higher exposure levels, However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level or duration to be effective, some embodiments described herein include a probe portion of the radiation pulse in addition to the therapeutic portion, the probe portion including radiation with a second intensity which is less than a first intensity at which the therapeutic portion is applied. In some instances, the second intensity may be less than the first intensity by a factor of 20-100 so as to provide a signal sufficient for reflection detection, but which does not result in further damage due to radiation.

More generally, the therapeutic portion of the radiation pulse may be at a relatively higher energy level than the subsequent probe portion of the radiation pulse, with the reflected radiation pulses of both the therapeutic portion and the probe portion being collected and converted to a photocurrent which may then be used to identify dynamics of the microbubbles in the RPE cells. In some instances, the dynamics may include an evaluation of the number, size, or depth of the microbubbles.

The real-time feedback may measure the dynamics of the microbubbles of the targeted RPE cells to the radiation pulses by measuring the formation, depth, size, and/or bursting of microbubbles that form on melanosomes of the targeted RPE cells in response to exposure to the therapeutic radiation. In an example embodiment, the formation and/or bursting of the microbubbles may be measured with optical feedback and/or acoustic feedback. In particular, the targeted RPE cells may reflect and/or emit optical and/or acoustic signals that may vary depending on the presence, absence, and/or characteristics (e.g., size, velocity) of the microbubbles. Excessive exposure to the therapeutic radiation after microbubble formation and RPE damage could damage other retinal structures, which may lead to formation of scotoma on the retina.

Figure 2:
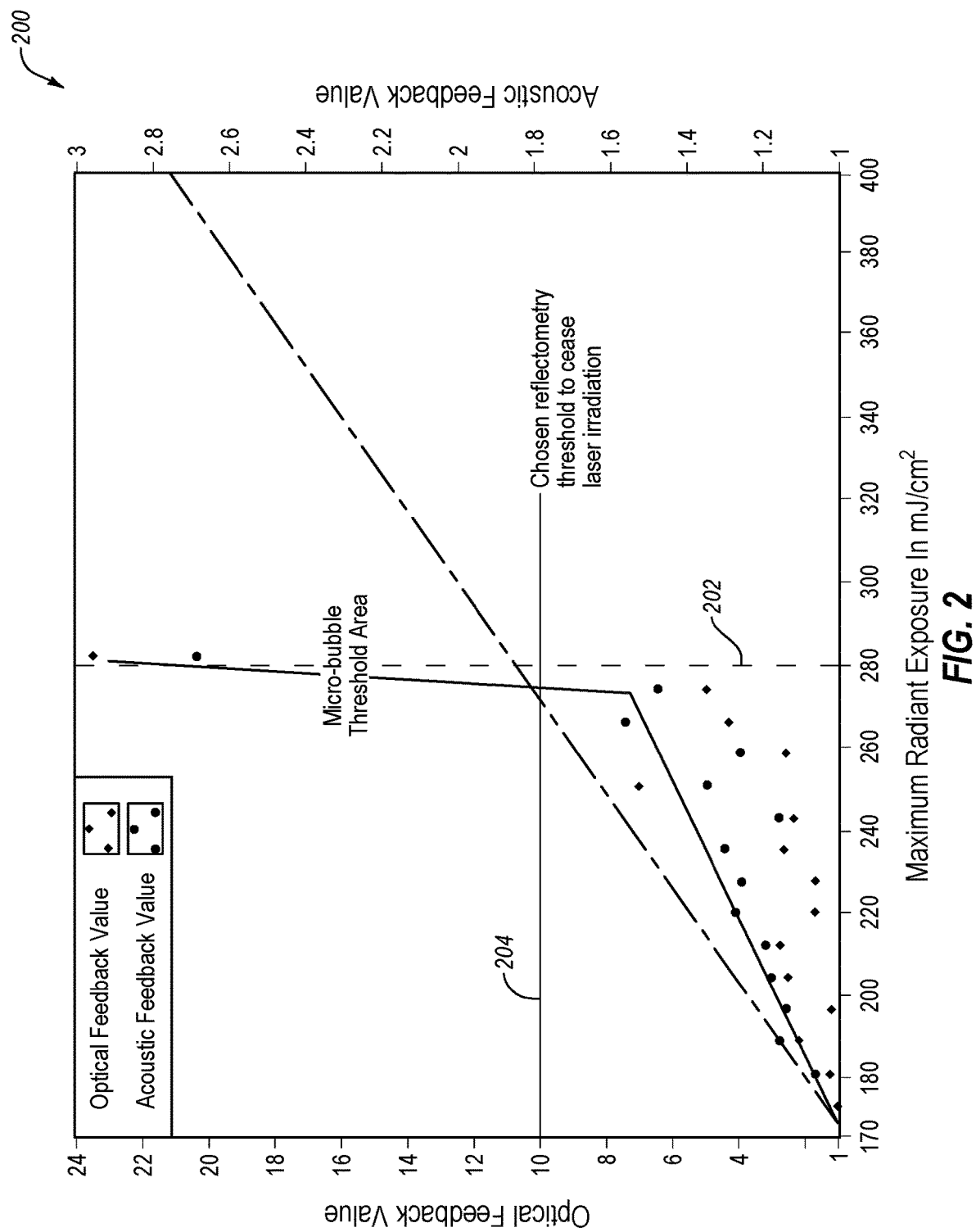
FIG. 2 is a graphical representation of an example feedback response to therapeutic radiation that may be generated by a laser-based ophthalmological surgical system.

FIG. 2 is a graphical representation 200 of an example feedback response to therapeutic radiation that may be generated by a laser-based ophthalmological surgical system, arranged in accordance with at least one embodiment described herein. The horizontal axis is radiant exposure to the therapeutic radiation in millijoules per square centimeter (mJ/cm$^2$), the left vertical axis is optical feedback value in microwatts, and the right axis is acoustic feedback value in volts. FIG. 2 includes data points representing the measured optical feedback (diamonds in FIG. 2) and acoustic feedback (circles in FIG. 2) as a function of therapeutic radiation exposure level. Each data point may represent a measurement of the optical or acoustic feedback from the targeted RPE cells and/or from microbubbles thereon after exposure to a pulse of the therapeutic radiation at a corresponding exposure level. All of the optical feedback data points may be collectively referred to as an optical signal and all of the acoustic feedback data points may be collectively referred to as an acoustic signal.

FIG. 2 additionally includes a vertical reference zone 202, at around 280 mJ/cm$^2$ in the example of FIG. 2, that represents a microbubble threshold area at a therapeutic radiation exposure level that may be known or expected to cause excessive damage to the targeted RPE cells. FIG. 2 additionally includes a horizontal reference line 204 at a threshold optical feedback value, at 10 arbitrary units (a.u.) in the example of FIG. 2, which may be selected as an optical feedback value after which irradiation with the therapeutic radiation may be terminated to avoid or reduce the likelihood of excessive damage to the targeted RPE cells.

The optical signal in the example of FIG. 2 may be generated by measuring reflected therapeutic radiation from the targeted RPE cells and/or from microbubbles that form thereon. As illustrated in FIG. 2, the optical signal in this example is somewhat noisy and exhibits substantial fluctuations, particularly around the vertical reference zone 202. This strong fluctuation in the measured optical signal may impose a difficulty in accurately determining when the optical signal is at or near the threshold optical feedback value.

Embodiments described herein may improve the accuracy of the feedback value by modifying the radiation pulses applied to the patient so as to include a probe portion, so as to provide improved feedback. Rather than directly using the reflected signal from the therapeutic portion of the radiation pulse, a probe radiation portion may be added to the radiation pulse in a laser-based ophthalmological surgical system. The probe radiation may be at a different wavelength than the therapeutic radiation. The probe radiation may be modulated at a modulation frequency. The probe radiation may be reflected by the RPE cells with or without the formation of micro-bubbles. A difference in the reflected signal from the probe radiation (the differential reflectometry signal) may be measured and may be used as a more accurate indicator for the formation of the micro-bubbles than the reflected signal from the therapeutic radiation. A gating technique may be deployed to collect the differential reflectometry signal. A lock-in amplifier technique may be optionally employed to further improve a signal-to-noise ratio in the reflectance measurement. Thus, the observed optical signal fluctuation illustrated in and described with respect to FIG. 2 may be suppressed.

Figure 3A:
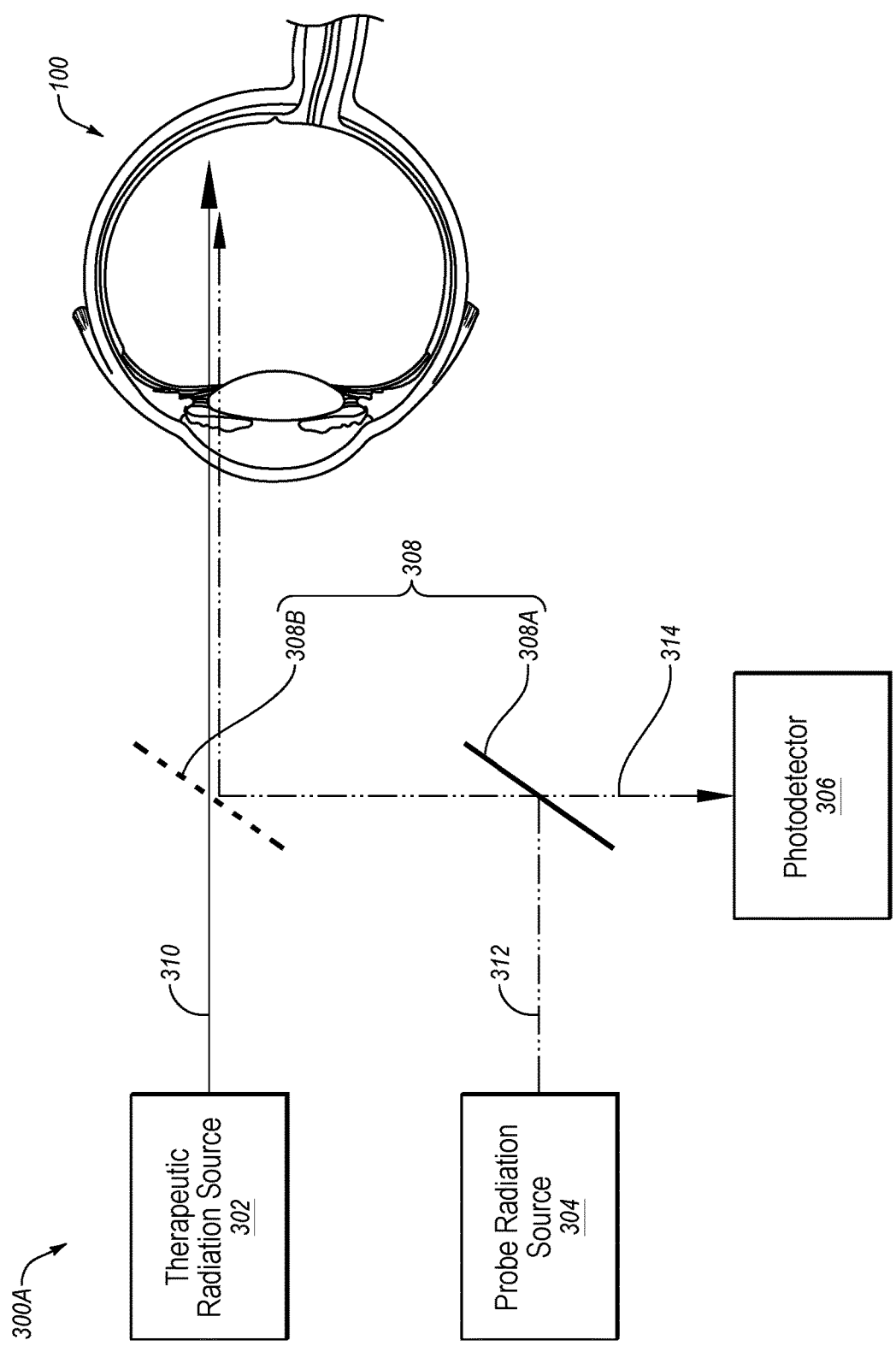
FIG. 3A is a block diagram of an example laser-based ophthalmological surgical system (hereinafter "system")

In more detail, FIG. 3A is a block diagram of an example laser-based ophthalmological surgical system (hereinafter "system") 300A, arranged in accordance with at least one embodiment described herein wherein the source of the therapeutic radiation portion of the radiation pulse is separate from the source of the probe radiation portion of the radiation pulse. More particularly, the system 300A may include a therapeutic radiation source 302, a probe radiation source 304, a photodetector 306, and one or more optical elements 308. The system may include one or more other elements not depicted in FIG. 3A for simplicity, such as one or more acoustic detectors, an imaging system (e.g., microscope), bias and/or modulation circuitry, and/or other elements.

The therapeutic radiation source 302 may be configured to emit therapeutic radiation 310 with a first wavelength. For instance, the therapeutic radiation 310 with the first wavelength may include therapeutic radiation with a center wavelength in a range from 430-500 nanometers (nm), or in a range from 520 nm to about 540 nm, such as 527 nm, or in a range from 575 nm or higher, such as 577 nm, or in some other range. The therapeutic radiation 310 in some embodiments may be pulsed, meaning the therapeutic radiation source 302 may emit the therapeutic radiation 310 as discrete pulses. The pulses of therapeutic radiation 310 may each have a pulse duration in a range from 1.6 microseconds to 1.8 microseconds.

Figure 4A:
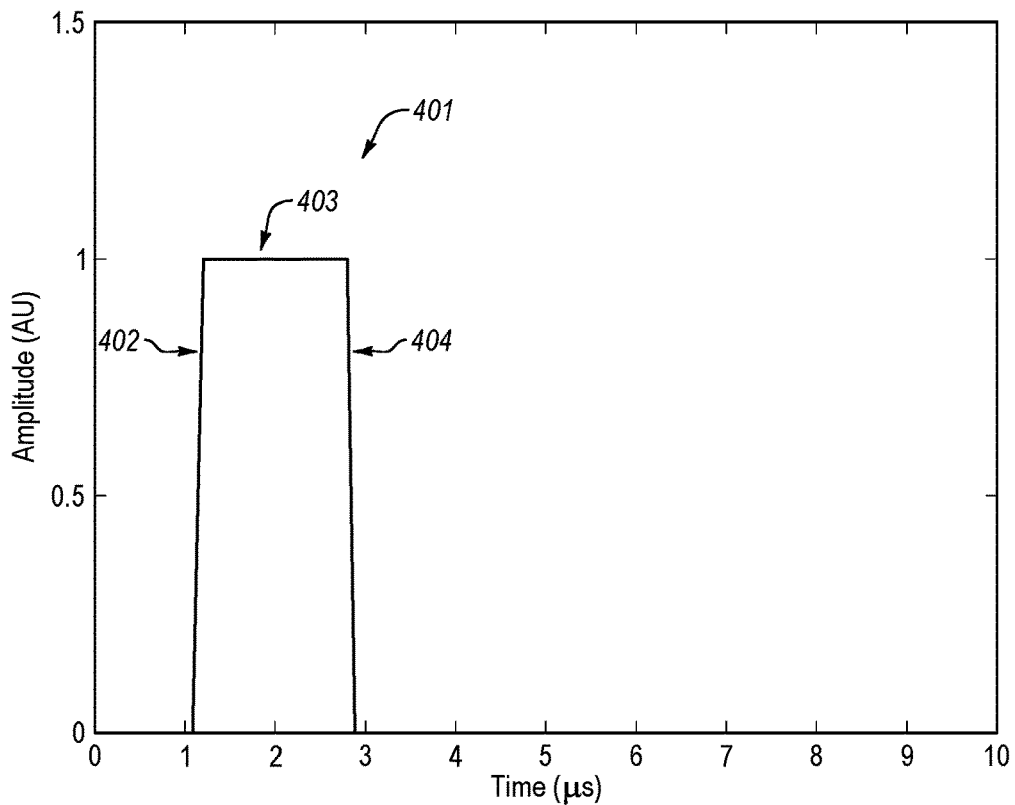
FIGS. 4A and 4B illustrate an example of a therapeutic portion of a radiation pulse that may be emitted by one or all of the systems of FIGS. 3A, 3B and 3C.

FIG. 4A shows a pulse of therapeutic radiation which may be currently used. As is shown in FIG. 4A, the pulses of therapeutic radiation 401 may be substantially flat-topped or may have some other shape. In some embodiments, the therapeutic radiation pulse 401 may have up to a maximum energy of at least 0.4 millijoules (mJ). The corresponding therapeutic radiation source may be controlled to emit discrete pulses of the therapeutic radiation pulse 401 that have an energy per pulse (hereinafter "pulse energy") in a range between 0 mJ up to the maximum energy. For instance, the discrete pulses of therapeutic radiation 401 may have a plateau shape including an increasing portion 402, wherein the energy is rapidly increased from 0 mJ up to the maximum energy, a plateau portion 403 in which the maximum energy is maintained for a predetermined period of time, and a decreasing portion 404, wherein the energy is rapidly decreased from the maximum energy.

Figure 4B:
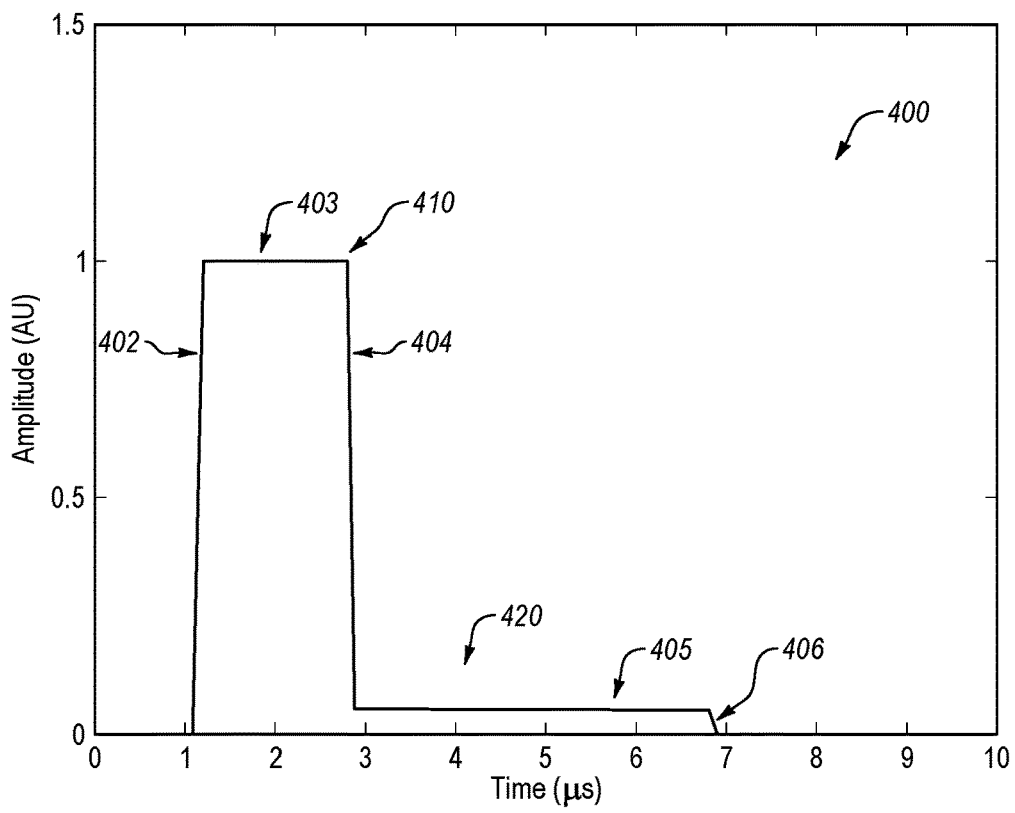

FIG. 4B illustrates radiation pulse 400 emitted by some systems and methods described herein which includes both a therapeutic radiation portion 410 and a probe radiation portion 420. As is shown in FIG. 4B, the therapeutic radiation portion 410 may have up to a maximum energy of at least 0.4 millijoules (mJ). The therapeutic radiation source 302 may be controlled to emit discrete pulses comprising the therapeutic radiation portion 410 of the radiation pulse 400 which have an energy per pulse (hereinafter "pulse energy") in a range between 0 mJ up to the maximum energy. For instance, the therapeutic radiation portion 410 may have a plateau shape including an increasing portion 402, wherein the energy is rapidly increased from 0 mJ up to the maximum energy, a plateau portion 403 in which the maximum energy is maintained for a predetermined period of time. Unlike the decreasing portion 404 of the standard pulse shown in FIG. 4A, which returns to 0 mJ, the decreasing portion 407 of the therapeutic radiation portion 410 comprises a portion wherein the energy is rapidly decreased as the probe radiation source 304 is configured to emit reflected radiation 312 with a second intensity at a plateau portion 405 that is different than the maximum intensity of the plateau portion 403 of the therapeutic radiation 310. After a predetermined period of time, the probe radiation source 304 is configured to decrease the intensity of the probe radiation at decreasing portion 406 and return the pulse to 0 mJ. As such, FIG. 4B corresponds to an aggregate radiation pulse applied by two separate components, namely, a therapeutic radiation source 302 and a probe radiation source 304.

In some embodiments, the probe radiation source 304 may include a targeting optical source already included in some legacy laser-based ophthalmological surgical systems and/or other laser-based ophthalmological surgical systems to optically align the therapeutic radiation source 302 to a target area of RPE cells in the eye 100 prior to irradiation with the therapeutic radiation 310. Such laser-based ophthalmological surgical systems may be modified to use the targeting optical source as the probe radiation source 304 as described herein. In these and other embodiments, the reflected radiation from the therapeutic radiation source 302 and the probe radiation source 304 can be detected and collected by the photodetector 306 generating a photocurrent from the collected reflected radiation pulses.

Alternatively, the photodetector 306 may be capable of differentiating between the reflected radiation pulse of the therapeutic radiation source 302 and the probe radiation source 304 and may only collect one portion to generate a corresponding photocurrent for further analysis. For example, the reflected radiation 312 may include radiation with a center wavelength in a red portion, e.g., 620 nm to 750 nm, of the visible spectrum, and/or in an orange portion, e.g., 590 nm to 620 nm, of the visible spectrum. As a particular example, the reflected radiation 312 with the second wavelength may include radiation with a center wavelength of 630 nm. Consequently, the photodetector 306 may only collect only a subset of the reflected radiation.

Similar to the therapeutic radiation 310, the reflected radiation 312 may be pulsed, or emitted as discrete pulses. In some embodiments, the discrete pulses of reflected radiation 312 may each have a pulse duration that is longer than the pulse duration of the discrete pulses of therapeutic radiation 310, as is shown in FIG. 4B. For instance, the probe portion 420 may each have a pulse duration in a range from four microseconds to sixteen microseconds, such as eight microseconds.

The one or more optical elements 308 may be configured to direct the therapeutic radiation 310 and the reflected radiation 312 into the eye 100 of a patient and to collect reflected radiation 314 from the eye 100 of the patient. As described elsewhere, the reflected radiation 314 may be indicative of an amount of therapeutic radiation exposure of the eye 100 of the patient. An area of the eye 100 to which the therapeutic radiation 310 is intended to be directed may be referred to as a target area. The one or more optical elements 308 may direct the therapeutic radiation 310 to the target area. The one or more optical elements 308 may also direct the reflected radiation 312 to at least a portion of the target area. Thus, the reflected radiation 312 may irradiate a first area within a second area irradiated by the therapeutic radiation 310 at overlapping and/or non-overlapping times.

The system 300A includes a first optical path of the reflected radiation 312 between the probe radiation source 304 and the eye 100. The system 300A additionally includes a second optical path of the therapeutic radiation 310 between the therapeutic radiation source 302 and the eye 100. In some embodiments, the one or more optical elements 308 may include a first beam splitter 308A and a second beam splitter 308B.

The first beam splitter 308A is positioned in the first optical path of the reflected radiation 312 between the probe radiation source 304 and the eye 100 of the patient. In the example of FIG. 3A, the first beam splitter 308A may be configured to reflect at least a portion of the reflected radiation 312 and the therapeutic radiation 310 from the probe radiation source 304 toward the eye 100 and to pass at least a portion of the reflected radiation 314 to the photodetector 306. In other embodiments, locations of the probe radiation source 304 and the photodetector 306 relative to the first beam splitter 308A may be swapped, as described with respect to FIG. 3B. In these and other embodiments, the first beam splitter 308A may include a 50/50 splitter at the second wavelength of the reflected radiation 312.

The second beam splitter 308B is positioned in the second optical path of the therapeutic radiation 310 between the therapeutic radiation source 302 and the eye 100 of the patient and in the first optical path between the first beam splitter 308A and the eye 100 of the patient. In the example of FIG. 3A, the second beam splitter 308B may be configured to pass at least a portion of the therapeutic radiation 310 from the therapeutic radiation source 302, reflect at least a portion of the reflected radiation 312 toward the eye 100 of the patient, and reflect at least a portion of the reflected radiation 314 collected from the eye 100 of the patient toward the first beam splitter 308A. In these and other embodiments, the second beam splitter 308B may include a dichroic splitter configured to pass the therapeutic radiation 310 at the first intensity and reflect the reflected radiation 312 and the reflected radiation 314, at the second intensity.

The photodetector 306 may be configured to receive the reflected radiation 314 from the one or more optical elements 308 and to generate a photocurrent indicative of the amount of therapeutic radiation exposure of the eye 100 of the patient. In these and other embodiments, a magnitude of the photocurrent may depend on an intensity or other characteristic of the reflected radiation 314, which in turn may depend on the presence, absence, and/or characteristics (e.g., size, velocity) of microbubbles, which in turn may depend on the therapeutic radiation exposure of the eye 100 of the patient. In some embodiments, the photodetector 306 may include a silicon-based positive-intrinsic-negative (PIN) diode, an avalanche photodiode (APD), or other suitable optical receiver.

Figure 3B:
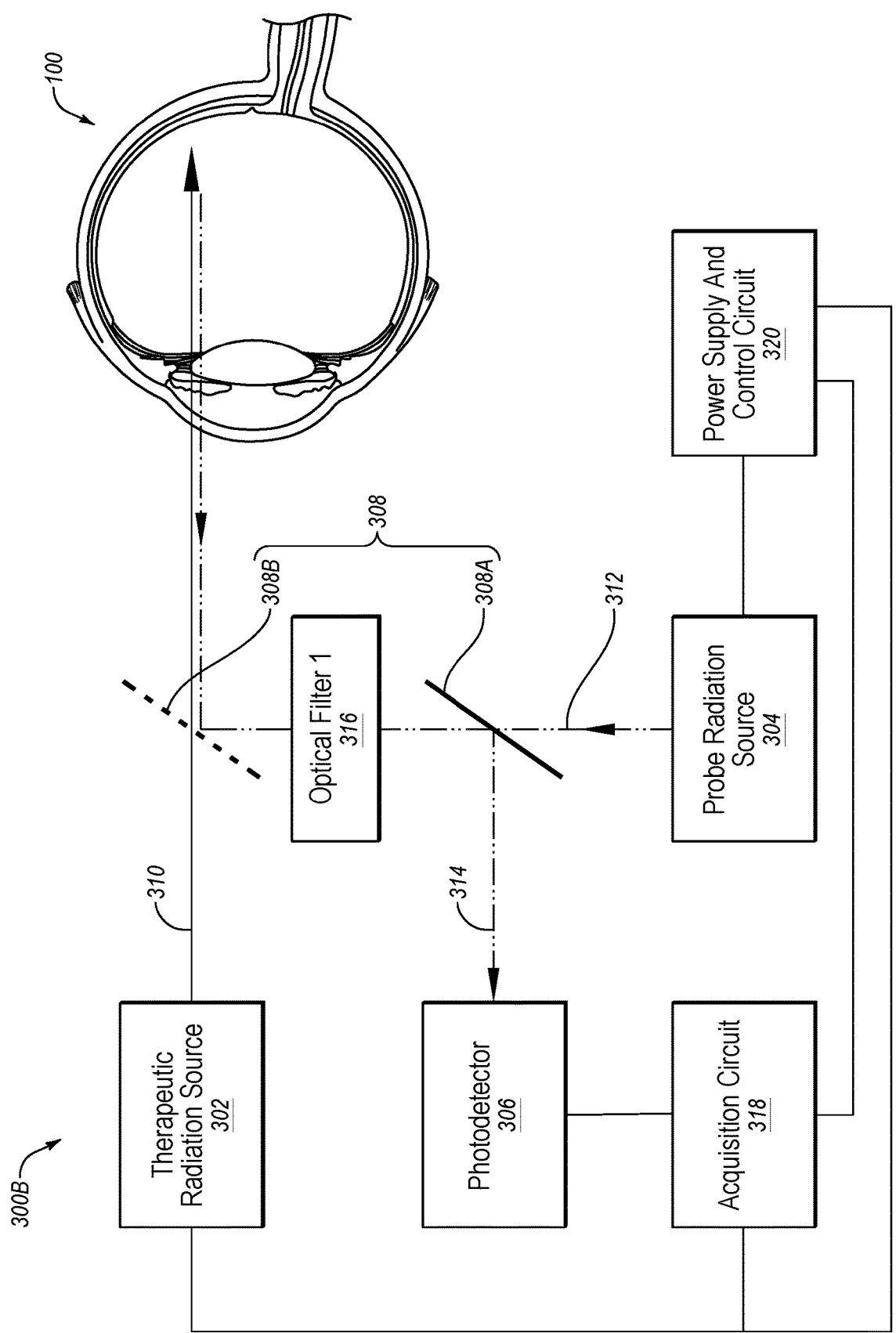
FIG. 3B is a block diagram of another example laser-based ophthalmological surgical system (hereinafter "system")

FIG. 3B is a block diagram of a combined, arranged in accordance with at least one embodiment described herein. The system 300B may include the therapeutic radiation source 302, the probe radiation source 304, the photodetector 306, and the one or more optical elements 308, all of which are generally operated and/or configured in a same or similar manner as in FIG. 3A. The system 300B may include one or more other elements not depicted in FIG. 3B for simplicity, such as one or more acoustic detectors, an imaging system (e.g., microscope), bias and/or modulation circuitry, and/or other elements.

Compared to FIG. 3A, in FIG. 3B, locations of the probe radiation source 304 and the photodetector 306 have been swapped relative to the first beam splitter 308A. Accordingly, in FIG. 3B, the first beam splitter 308A may be configured to pass at least a portion of the reflected radiation 312 from the probe radiation source 304 and to reflect at least a portion of the reflected radiation 314 toward the photodetector 306.

Compared to FIG. 3A, the system 300B of FIG. 3B may further include one or more of an optical filter 316, an acquisition circuit 318, and a power supply and control circuit 320.

As illustrated in FIG. 3A, the optical filter 316 may be positioned in the first optical path between the first beam splitter 308A and the second beam splitter 308B. The optical filter 316 may be configured to pass the reflected radiation 312 and the reflected radiation 314 and to block the therapeutic radiation 310 from passing. For instance, the optical filter 316 may have a transmittance of at least 70%, 80%, 90%, 95%, or higher with respect to the reflected radiation 314 and may have a transmittance less than 10%, 5%, or lower with respect to the therapeutic radiation 310.

The acquisition circuit 318 may be electrically coupled to at least one of the therapeutic radiation source 302 (or a control circuit of the therapeutic radiation source), the photodetector 306, and the power supply and control circuit 320. The acquisition circuit 318 may be configured to process and/or convert photocurrent generated by the photodetector 306 to one or more optical feedback values, such as the optical feedback values graphically illustrated in FIG. 2. The acquisition circuit 318 may be configured to gate the photodetector 306 according to expected time intervals of microbubble formation and/or bursting. For instance, the acquisition circuit 318 may gate the photodetector 306 so that the photodetector 306 generates photocurrent only during expected time intervals of microbubble formation and/or bursting without generating photocurrent during other time intervals.

The therapeutic radiation source 302 may include or be coupled to a control circuit (not shown separately) of the therapeutic radiation source 302 to which the acquisition circuit 318 may also be electrically coupled. The control circuit of the therapeutic radiation source 302 may be configured to operate the therapeutic radiation source 302 and to the probe radiation source 304 to emit the therapeutic radiation portion 310 and the probe radiation portion 304 of the radiation pulse. The control circuit of the therapeutic radiation source 302 may generate and send a trigger signal to the acquisition circuit 318. The trigger signal may indicate when the therapeutic radiation portion 310 is being emitted. The acquisition circuit 318 may be configured to receive the trigger signal from the control circuit of the therapeutic radiation source 302 to gate the photodetector 306 to generate photocurrent beginning when the therapeutic radiation source begins emitting the therapeutic radiation portion and terminating after a duration corresponding to an end of the probe radiation portion 304. The duration during which the photodetector 306 is gated to generate photocurrent may be in a range from four microseconds to sixteen microseconds, such as eight microseconds.

Although in the embodiments described above, the therapeutic radiation source 302 and the probe radiation source 304 are described as separate components, they may be a single radiation source which supplies a single radiation pulse, such as the pulse supplied in FIG. 4B, by lowering intensity at which the single radiation source operates at a first level 403 for a period of time corresponding to, for instance 1.6 to 1.8 microseconds, to a second level 405 for a second period of time, of two to four additional microseconds.

Figure 3C:
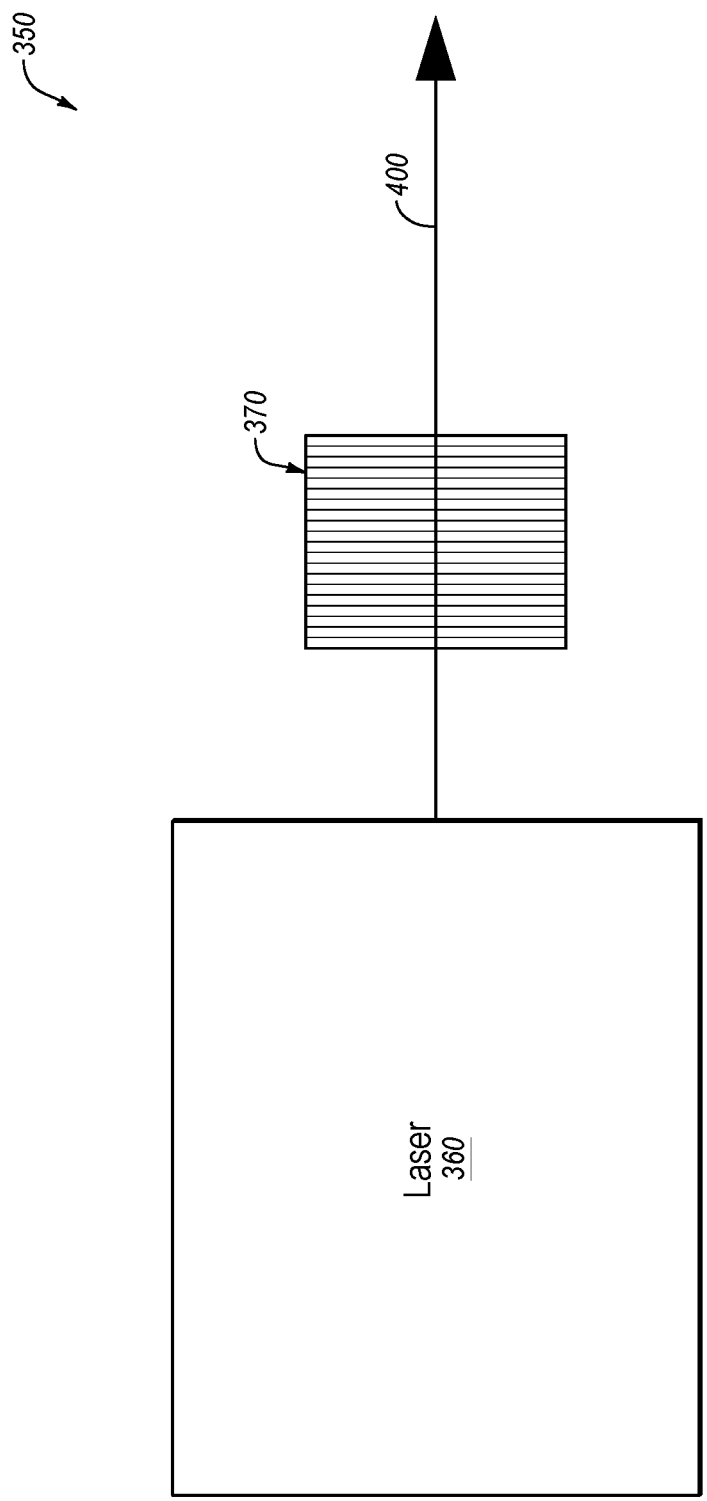
FIG. 3C is a block diagram of another example laser-based ophthalmological surgical system (hereinafter "system")

FIG. 3C illustrates one example of a single radiation source 350 which supplies both the therapeutic portion 410 and the probe portion 420 of the radiation pulse. The radiation source or laser 350, comprises a laser or radiation source 360 and a resonant cavity 370. The single radiation source 350 may be operated by operating the single radiation source in two stages, such that in the first stage, corresponding to the therapeutic portion 410, the radiation source 350 is operated at a first intensity to obtain a maximum intensity 403 which is applied for approximately 1.7 microseconds, as shown in FIG. 4B, and a second stage, corresponding to the probe portion 420, the intensity of the radiation source 302 is reduced by a factor of 20-100 so as to provide a reflected radiation 312.

In this embodiment, the probe portion 420 of the radiation pulse is obtained by operating the resonant cavity 370 for the second stage of the radiation pulse. In one embodiment, the resonant cavity 370 is a Fabry-Pérot etalon and/or a very high Q resonant cavity. The optical signal output of a very high Q resonant cavity such as the resonant cavity 370 where the optical input signal is a pulse may primarily be the impulse response of the cavity. The duration of the impulse response may be inversely related to the Q factor of the cavity and may indicate the duration in which an optical pulse is contained in the cavity. In another example, the resonant cavity 370 can be a sphere supporting whispering gallery modes. To achieve the required pulse length of 4 microseconds the resonant cavity 370 has an effective length of c (speed of light)×4e-6=1200 m. More particularly, in some embodiments, the resonant cavity 370 has a length of 10 cm and mirrors with a reflection of 0.999.

Although in FIG. 3C, the resonant cavity 270 is shown as being optically connected to the radiation source 360 to the resonant cavity 370, other embodiments may include optical components for redirecting the radiation pulse from the radiation source 360 such that during the therapeutic portion 410 of the radiation pulse 400, the radiation pulse 400 at the first intensity is directed to the eye of the patient without passing through the resonant cavity 370, whereas during the probe portion 420 of the radiation pulse 400, the radiation pulse 400 at the first intensity is redirected via various optical components to the resonant cavity 370 where it is modulated to the second intensity prior to being directed to the eye of the patient.

Returning to FIGS. 3A-3B, the systems 300A, 300B may implement any suitable detection scheme to detect the reflected radiation 314. In embodiment, this measured quantity may then be used to indicate dynamics of microbubbles in the RPE cells.

Figure 5A:
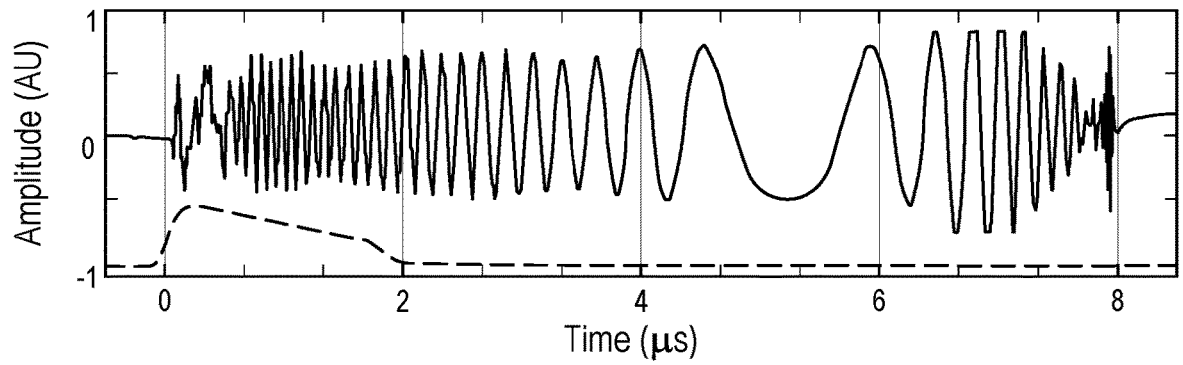
FIGS. 5A-5C illustrate dynamics of the microbubbles in the RPE cells that may be identified by one or all of the systems of FIGS. 3A, 3B, and 3C.
Figure 5B:
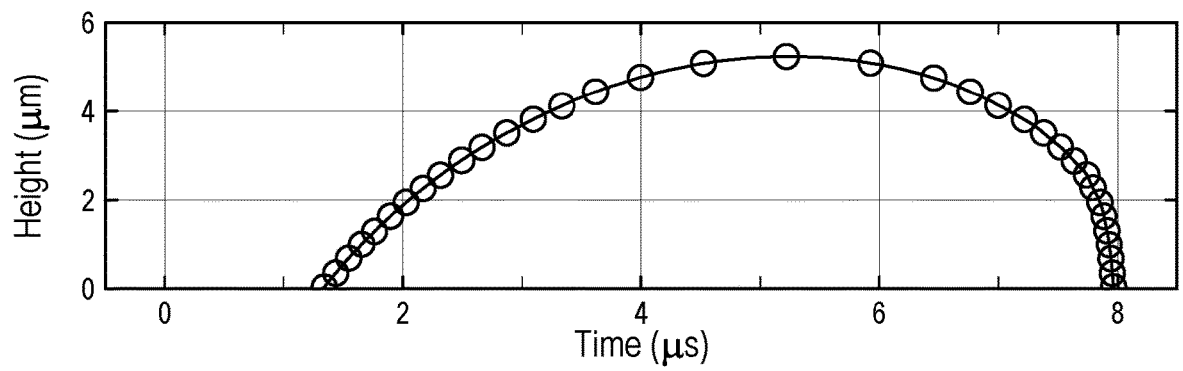
Figure 5C:
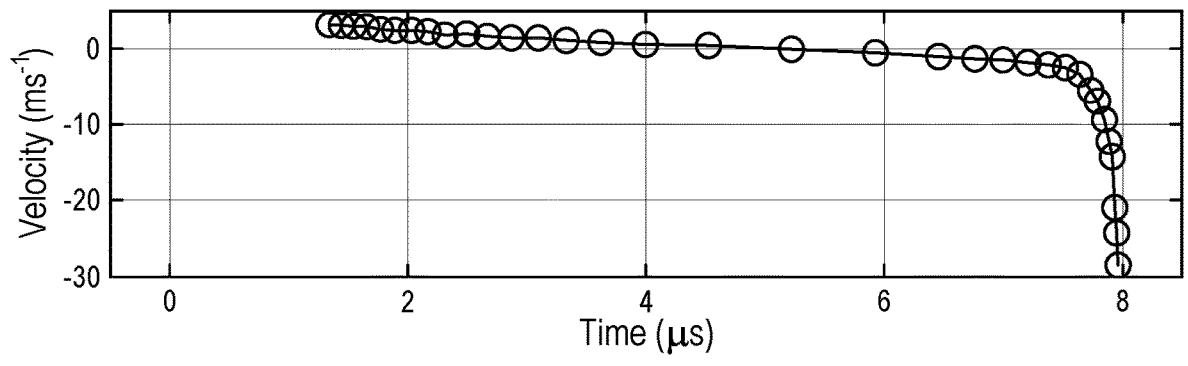

FIGS. 5A, 5B, 5C illustrate the dynamics of a microbubble which may be measured or identified based on the collected reflected radiation 314. As is shown in FIG. 5A, the reflected radiation 314 may be used to identify a height or amplitude of a microbubble as a function of time. Furthermore, the reflected radiation 314 may be used to identify a height or depth to which a microbubble is formed as a function of time, as is shown in FIG. 5B. Furthermore, the reflected radiation 314 may be used to identify a velocity of the microbubble's wall as a function of time as the microbubble forms, expands, and eventually collapses or bursts as is shown in FIG. 5C.

Figure 5D:
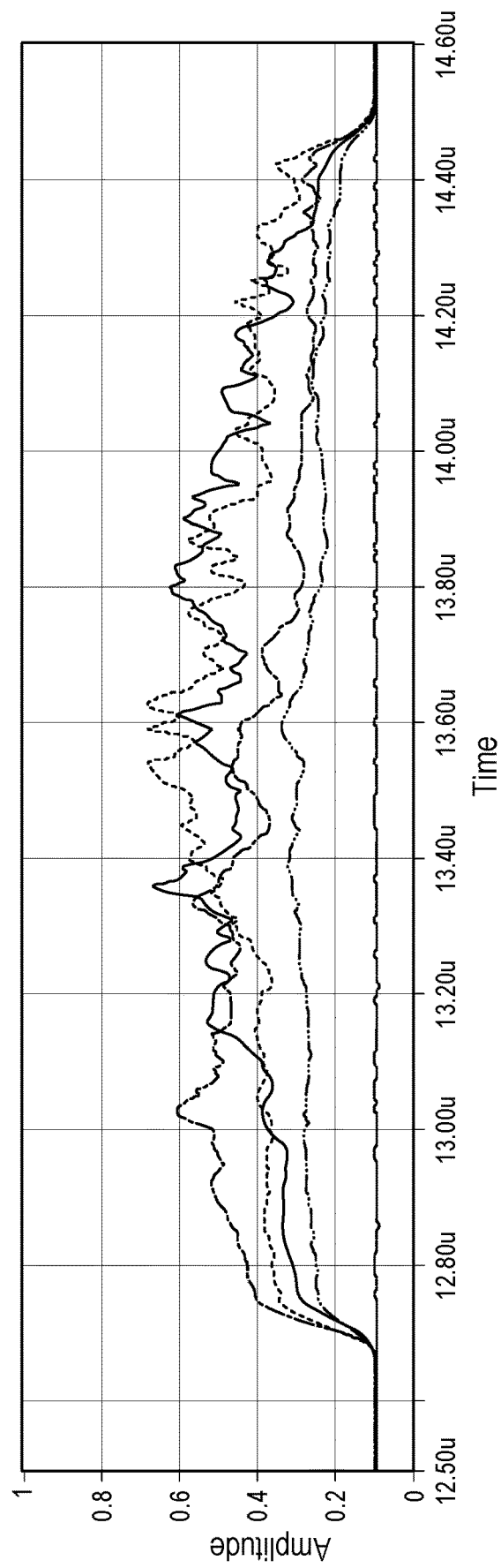
FIG. 5D illustrates a back reflected signal typically available using dosimetry.

In contrast to the dynamics which may be available using some of the systems and methods described herein, such as are illustrated in FIGS. 5A-5C, FIG. 5D illustrates the back reflected signal typically available using dosimetry. As is shown in FIG. 5D, because the typical duration of the therapeutic radiation pulse is approximately 2 microseconds, the reflected pulse has a corresponding duration of approximately 2 microseconds such that only a subset of the microbubble dynamics may be captured when relying on only the reflected radiation from the therapeutic radiation pulse. One difficulty with this method is that many microbubbles reach a peak height after 4 microseconds and collapse after 6 microseconds as can be seen from FIGS. 5A-5C, both of which may occur 2-4 microseconds after a typical therapeutic radiation pulse has concluded and the reflected pulse has terminated. Consequently, information corresponding to the microbubbles throughout their duration may be unavailable when relying on back-reflected signals such as those of FIG. 5D.

In contrast, because the radiation pulse 400 includes the probe radiation portion 420 in addition to the therapeutic radiation portion 410, the duration at which a radiation signal is applied is extended and consequently the duration at which the radiation pulse can be reflected and subsequently analyzed is extended. Hence, the systems and methods described herein provide an enhanced optical detection of microbubbles by expanding the duration of the radiation pulse.

Figure 6:
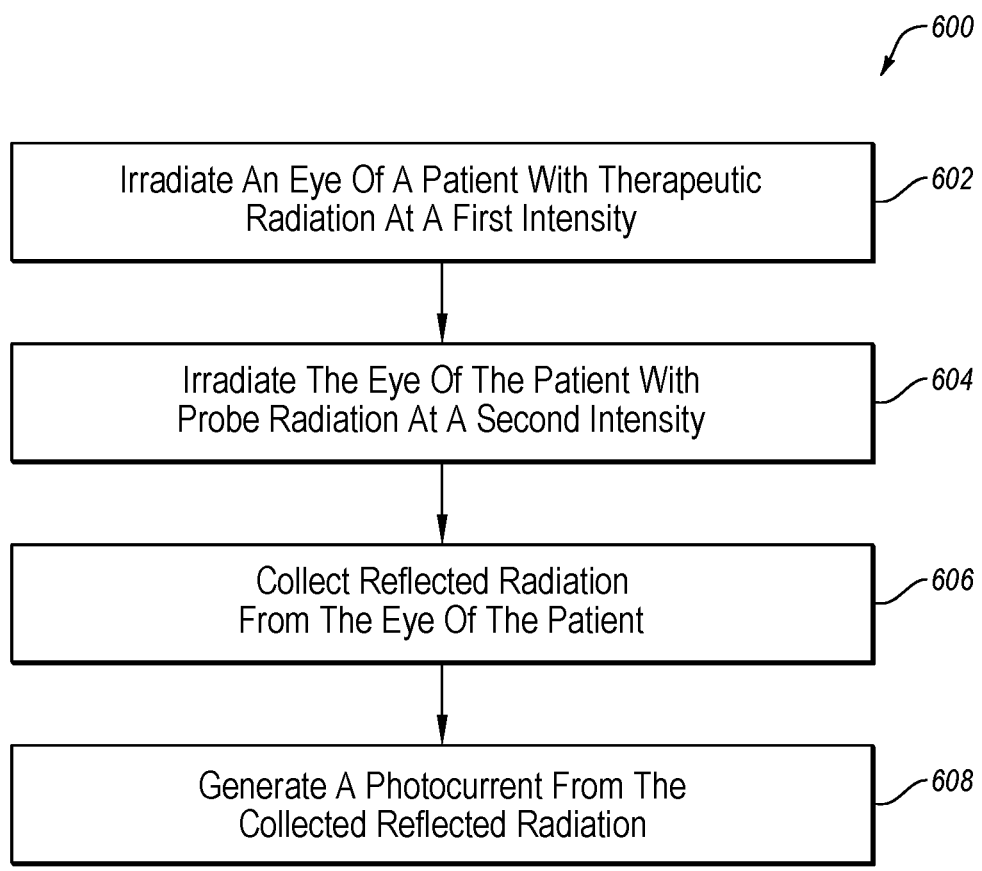
FIG. 6 illustrates a flow diagram of an example method to measure therapeutic radiation dosimetry.

FIG. 6 illustrates a flow diagram of an example method 600 to measure therapeutic radiation dosimetry, arranged in accordance with at least some embodiments described herein. The method 600 may be performed, in whole or in part, in the systems 300A, 300B, 350 and/or in other systems and configurations. Alternatively or additionally, the method 600 may be implemented by a processor device that performs or controls performance of one or more of the operations of the method 600. For instance, a computer (such as the computing device 700 of FIG. 7) or other processor device may be communicatively coupled to the system 300A or 300B and may execute software or other computer-readable instructions accessible to the computer, e.g., stored on a non-transitory computer-readable medium accessible to the computer, to perform or control the system 300A or 300B to perform the method 600 of Figure.

The method 600 may include one or more of blocks 602, 604, 606, and/or 608. Although illustrated as discrete blocks, various blocks may be divided into additional blocks, supplemented with additional blocks, combined into fewer blocks, or eliminated, depending on the particular implementation. The method 600 may begin at block 602.

In block 602 ("Irradiate An Eye Of A Patient With Therapeutic Radiation At A First Intensity"), an eye of a patient may be irradiated with therapeutic radiation at a first intensity. The therapeutic radiation may cause microbubbles to form on melanosomes of RPE cells of the eye of the patient. The therapeutic radiation may include, e.g., the therapeutic radiation 310 of FIGS. 3A-3C or the therapeutic portion 410 of a radiation pulse 400 shown in FIG. 3C. Block 602 may be followed by block 604.

In block 604 ("Irradiate The Eye Of The Patient With Probe Radiation At A Second Intensity"), the eye of the patient may be irradiated with probe radiation with a second intensity which is less than the first intensity. The probe radiation may include, e.g., the reflected radiation 312 of FIGS. 3A-3B or the probe portion 420 of a radiation pulse 400 shown in FIG. 3C. Block 604 may be followed by block 606.

In block 606 ("Collect Reflected Radiation From The Eye Of The Patient"), reflected radiation may be collected from the eye of the patient. The reflected radiation may include, e.g., the reflected radiation 314, 512, or 518 of FIGS. 3A-3B. Block 606 may be followed by block 608.

In block 608 ("Generate A Photocurrent From The Collected Reflected Radiation"), a photocurrent may be generated from the collected reflected radiation. The photocurrent may be indicative of dynamics of the microbubbles in the RPE cells of the eye of the patient.

For this and other procedures and methods disclosed herein, the functions or operations performed in the processes and methods may be implemented in differing order. Furthermore, the outlined operations are only provided as examples, and some of the operations may be optional, combined into fewer operations, supplemented with other operations, or expanded into additional operations without detracting from the disclosed embodiments.

In an embodiment of the method 600, irradiating the eye of the patient may entail irradiating the eye of the patient with the therapeutic portions 410 having a duration of not more than two microseconds.

In an embodiment of the method 600, irradiating the eye of the patient may entail irradiating the eye of the patient with the probe portions 420 having a duration in a range from two to four microseconds.

In an embodiment of the method 600, irradiating the eye of the patient includes irradiating the eye of the patient with the radiation pulses that each comprise the probe portion 420 with the second intensity that is in a range from $1/100$ to $1/20$ of the first intensity of the therapeutic portion 410.

In an embodiment of the method 600, the method 600 also includes modulating a therapeutic radiation source 360 with a modulation signal configured to cause the therapeutic radiation source 360 to emit the radiation pulses that each include both the therapeutic portion 410 and the probe portion 420.

In an embodiment of the method 600, modulating the therapeutic radiation source 360 with the modulation signal includes alternately modulating the therapeutic radiation source 360 at least at a first signal level or higher and at a second signal level that is lower than the first signal level, the first signal level is configured to cause the therapeutic radiation source 360 to emit the therapeutic portions 410 of the radiation pulses 400, and the second signal level is configured to cause the therapeutic radiation source 360 to emit the probe portions 420 of the radiation pulses 400.

In an embodiment of the method 600, the method also includes modulating the therapeutic radiation source 360 with a modulation signal configured to cause the therapeutic radiation source 360 to emit the therapeutic portions 410 of the radiation pulses 400, and optically coupling the therapeutic radiation source 350 of the radiation pulses to a resonant cavity 370. In such embodiments, the resonant cavity 370 is configured to emit the probe portions 420 of the radiation pulses 400 following the therapeutic portions 410, and irradiating the eye of a patient with the radiation pulses 400 comprises directing both the therapeutic portions 410 emitted by the therapeutic radiation source 360 and the probe portions 420 emitted by the resonant cavity 370 into the eye of the patient.

In an embodiment of the method 600, optically coupling the therapeutic radiation source 360 of the radiation pulses to the resonant cavity 370 comprises optically coupling the therapeutic radiation source 360 of the radiation pulses 400 into a Fabry-Pérot etalon.

In an embodiment of the method 600, optically coupling the therapeutic radiation source 360 of the radiation pulses 400 into the Fabry-Pérot etalon includes optically coupling the therapeutic radiation source 360 of the radiation pulses 400 into the Fabry-Pérot etalon having end mirrors each with a reflectivity greater than 99%.

In an embodiment of the method 600, optically coupling the therapeutic radiation source 360 of the radiation pulses 400 into the resonant cavity comprises optically coupling the therapeutic radiation source of the radiation pulses into a spherical resonant cavity that supports whispering gallery modes.

In an embodiment of the method 600, the method includes determining an exposure level of the eye of the patient to the radiation pulses 400 based on the generated photocurrent, and terminating exposure of the eye of the patient to the radiation pulses 400 in response to the exposure level of the eye of the patient to the radiation pulses reaching a threshold exposure level.

Figure 7:
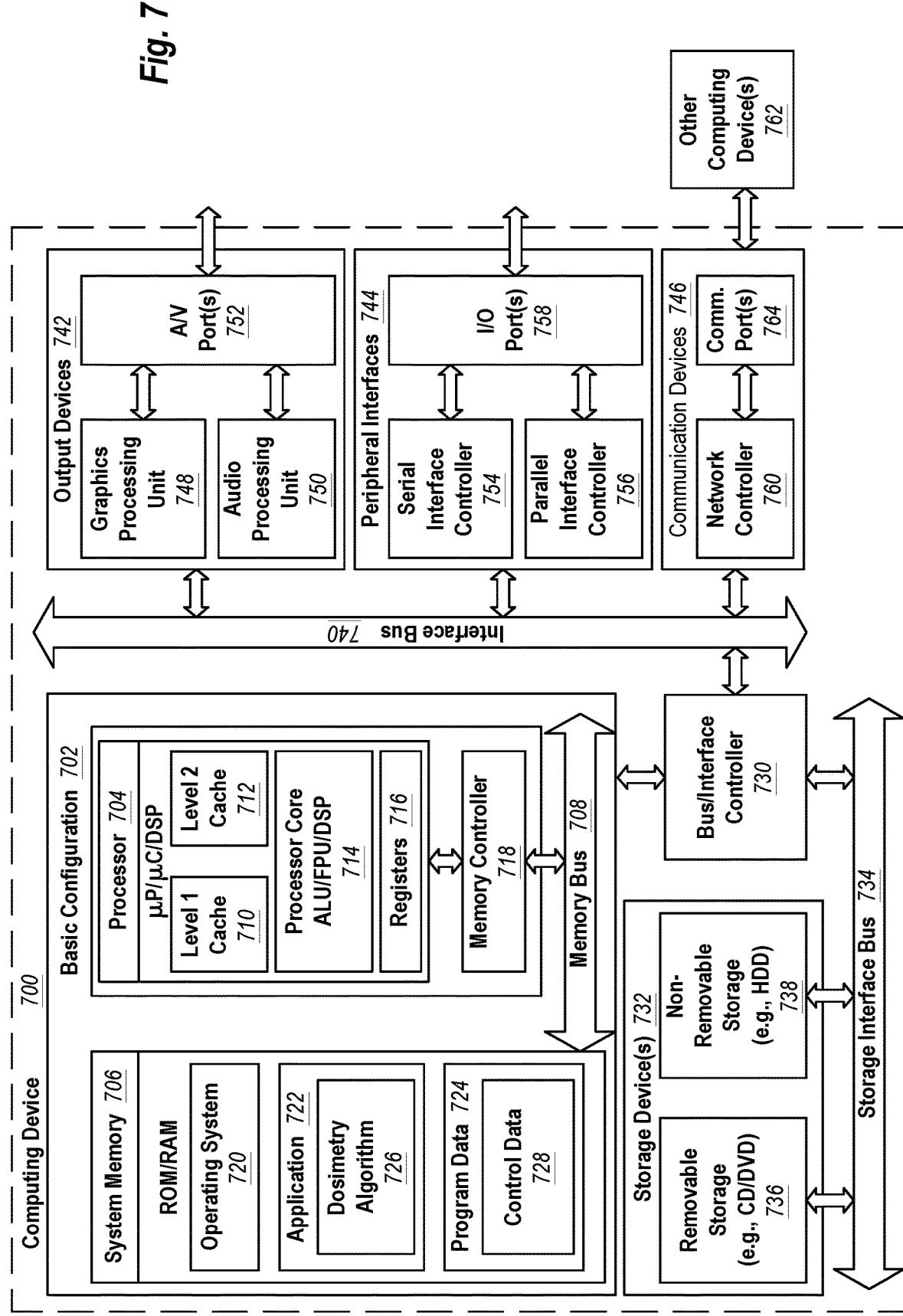
FIG. 7 illustrates a block diagram of an example computing device, all arranged in accordance with at least one embodiment of the present disclosure.

FIG. 7 illustrates a block diagram of an example computing device 700, in accordance with at least one embodiment of the present disclosure. The computing device 700 may be used in some embodiments to perform or control performance of one or more of the methods and/or operations described herein. For instance, the computing device may be communicatively coupled to and/or included in the system 300A or 300B of FIG. 3A or 3B to perform or control performance of the method 600 of FIG. 6. In a basic configuration 702, the computing device 700 typically includes one or more processors 704 and a system memory 706. A memory bus 708 may be used for communicating between the processor 704 and the system memory 706.

Depending on the desired configuration, the processor 704 may be of any type including, such as a microprocessor (μP), a microcontroller (μC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations, the memory controller 718 may be an internal part of the processor 704.

Depending on the desired configuration, the system memory 706 may be of any type, such as volatile memory (such as RAM), non-volatile memory (such as ROM, flash memory, or the like), or any combination thereof. The system memory 706 may include an operating system 720, one or more applications 722, and program data 724. The application 722 may include a dosimetry algorithm 726 that is arranged to measure therapeutic radiation dosimetry. The program data 724 may include control data 728 such as bias values to bias the therapeutic and/or probe radiation sources, pulse repetition rates, pulse durations, pulse train repetition rates, pulse train durations, and/or other data that may be used to control aspects of the therapeutic and/or probe radiation emitted by the system 300A or 300B of FIGS. 3A-3B. In some embodiments, the application 722 may be arranged to operate with the program data 724 on the operating system 720 to perform one or more of the methods and/or operations described herein, including those described with respect to FIG. 6.

The computing device 700 may include additional features or functionality, and additional interfaces to facilitate communications between the basic configuration 702 and any other devices and interfaces. For example, a bus/interface controller 730 may be used to facilitate communications between the basic configuration 702 and one or more data storage devices 732 via a storage interface bus 734. The data storage devices 732 may include removable storage devices 736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer-readable instructions, data structures, program modules, or other data.

The system memory 706, the removable storage devices 736, and the non-removable storage devices 738 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752. The peripheral interfaces 744 include a serial interface controller 754 or a parallel interface controller 756, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 758. The communication devices 746 include a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 700 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. It is also to be understood that the terminology used herein is for the purpose of describing particular embodiments only, and is not intended to be limiting.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A method of therapeutic radiation dosimetry to an eye of a patient, the method comprising:
   irradiating the eye of the patient with radiation pulses on a treatment location, wherein each radiation pulse includes a therapeutic portion and a probe portion, the therapeutic portion being immediately followed by the probe portion to form a single aggregate pulse, the therapeutic portion having at least a first intensity and the probe portion having a second intensity less than the first intensity, wherein each therapeutic portion of each radiation pulse is configured to cause microbubbles to form on melanosomes of retinal pigment epithelial (RPE) cells of the eye of the patient;
   collecting reflected radiation pulses from the treatment location of the eye of the patient, wherein each reflected radiation pulse includes a reflected therapeutic portion and a reflected probe portion; and
   generating a photocurrent from the collected reflected radiation pulses, the photocurrent being indicative of dynamics of the microbubbles in the RPE cells of the eye of the patient.

2. The method of claim 1, further comprising at least one of:
   providing the therapeutic portion of each radiation pulse to the eye during irradiating for a duration of two microseconds or less; or providing the probe portion of each radiation pulse to the eye during the irradiating for a duration in a range from about two to about four microseconds.

3. The method of claim 1, further comprising providing each radiation pulse to have the probe portion with the second intensity in a range from $1/100$ to $1/20$ of the first intensity of the therapeutic portion.

4. The method of claim 1, further comprising modulating a therapeutic radiation source with a modulation signal configured to cause the therapeutic radiation source to emit the radiation pulses that each include both the therapeutic portion and probe portion.

5. The method of claim 1, further comprising modulating a therapeutic radiation source with a modulation signal that includes alternately a first signal level and a second signal level that is lower than the first signal level, wherein:
   the first signal level is configured to cause the therapeutic radiation source to emit the therapeutic portion of each radiation pulse; and
   the second signal level is configured to cause the therapeutic radiation source to emit the probe portion of each radiation pulse.

6. The method of claim 1, further comprising:
   modulating a therapeutic radiation source with a modulation signal configured to cause the therapeutic radiation source to emit the therapeutic portion of each radiation pulse; and
   optically coupling the therapeutic radiation source to a resonant cavity, that is configured to emit the probe portion of each radiation pulse following the therapeutic portion; and
   directing both the therapeutic portion emitted by the therapeutic radiation source and the probe portions emitted by the resonant cavity into the eye of the patient.

7. The method of claim 1, further comprising optically coupling a therapeutic radiation source that emits the radiation pulses into a resonant cavity by optically coupling the therapeutic radiation source into a Fabry-Pérot etalon, the Fabry-Pérot etalon having end mirrors each with a reflectivity greater than 99%.

8. The method of claim 1, further comprising optically coupling a therapeutic radiation source that emits the radiation pulses into a resonant cavity by optically coupling the therapeutic radiation source into a spherical resonant cavity that supports whispering gallery modes.

9. The method of claim 1, further comprising:
   determining an exposure level of the eye of the patient to the radiation pulses based on the generated photocurrent; and
   terminating exposure of the eye of the patient to the radiation pulses in response to the exposure level of the eye of the patient to the radiation pulses reaching a threshold exposure level.

10. A laser-based ophthalmological surgical system, comprising:
    a therapeutic radiation source configured to emit radiation pulses, wherein each radiation pulse includes a therapeutic portion and a probe portion, the therapeutic portion being immediately followed by the probe portion to form a single aggregate pulse, the therapeutic portion having at least a first intensity and the probe portion having a second intensity less than the first intensity, wherein the therapeutic portion is configured to cause microbubbles to form on melanosomes of retinal pigment epithelial (RPE) cells of an eye of a patient;
    one or more optical elements configured to direct the radiation pulses into a treatment location of the eye of the patient and to collect reflected radiation pulses from the treatment location of the eye of the patient, wherein each reflected radiation pulse includes a reflected therapeutic portion and a reflected probe portion; and
    a photodetector configured to receive the reflected radiation pulses from the one or more optical elements and to generate from the reflected radiation pulses a photocurrent indicative of dynamics of the microbubbles in the RPE cells of the eye of the patient.

11. The laser-based ophthalmological surgical system of claim 10, wherein the therapeutic radiation source is configured to emit the radiation pulses that include at least one of:
    the therapeutic portion of each radiation pulse includes. a duration of two microseconds or less; or
    the probe portion of each radiation pulse includes a duration in a range from about two to four about microseconds.

12. The laser-based ophthalmological surgical system of claim 10, wherein the therapeutic radiation source is configured to emit the probe portion with the second intensity in a range from 1/100 to 1/20 of the first intensity of the therapeutic portion.

13. The laser-based ophthalmological surgical system of claim 10, further comprising a modulation circuit operably coupled to the therapeutic radiation source and configured to modulate the therapeutic radiation source with a modulation signal to cause the therapeutic radiation source to emit the radiation pulses.

14. The laser-based ophthalmological surgical system of claim 10, further comprising a modulation circuit configured to provide a modulation signal that alternates between a first signal level and a second signal level that is lower than the first signal level, wherein:
  the first signal level is configured to cause the therapeutic radiation source to emit the therapeutic portion of each radiation pulse; and
  the second signal level is configured to cause the therapeutic radiation source to emit the probe portions of each radiation pulse.

15. The laser-based ophthalmological surgical system of claim 10, further comprising a resonant cavity optically coupled to the therapeutic radiation source and configured to receive the therapeutic portion of each radiation pulse and to emit the probe portion following the therapeutic portion.

16. The laser-based ophthalmological surgical system of claim 10, further comprising a resonant cavity optically coupled to the therapeutic radiation source, wherein the resonant cavity includes a Fabry-Pérot etalon or a spherical resonant cavity that supports whispering gallery modes.

17. The laser-based ophthalmological surgical system of claim 10, further comprising a resonant cavity that includes a Fabry-Pérot etalon optically coupled to the therapeutic radiation source, wherein the Fabry-Pérot etalon comprises end mirrors each with a reflectivity greater than 99%.

18. The laser-based ophthalmological surgical system of claim 10, further comprising a resonant cavity that includes a Fabry-Pérot etalon optically coupled to the therapeutic radiation source, wherein the Fabry-Pérot etalon has an effective length equal to $c*t_{pulse}$, wherein c is the speed of light in a vacuum and $t_{pulse}$ is a duration of each radiation pulse in a range from about two to about four microseconds.

19. The laser-based ophthalmological surgical system of claim 10, further comprising a processor communicatively coupled to the photodetector and the therapeutic radiation source, wherein the processor is configured to perform or control performance of the system to:
  determine an exposure level of the eye of the patient to the radiation pulses based on the generated photocurrent; and
  terminate exposure of the eye of the patient to the radiation pulses in response to the exposure level reaching a threshold exposure level.

20. The laser-based ophthalmological surgical system of claim 10, wherein the surgical system is configured to detect RPE damage by collecting the reflected radiation pulses from the treatment location of the eye of the patient to perform a real-time feedback.

21. A method of therapeutic radiation dosimetry to an eye of a patient, the method comprising:
  irradiating the eye of the patient with radiation pulses on a treatment location, wherein each radiation pulse includes a therapeutic portion with at least a first intensity followed by a probe portion with a second intensity less than the first intensity, wherein each therapeutic portion of each radiation pulse is configured to cause microbubbles to form on melanosomes of retinal pigment epithelial (RPE) cells of the eye of the patient;
  detecting RPE damage by collecting reflected radiation pulses from the treatment location of the eye of the patient to perform a real-time feedback, wherein each reflected radiation pulse includes a reflected therapeutic portion and a reflected probe portion; and
  generating a photocurrent from the collected reflected radiation pulses, the photocurrent being indicative of dynamics of the microbubbles in the RPE cells of the eye of the patient.

* * * * *